(12) United States Patent
Belalcazar et al.

(10) Patent No.: US 8,131,356 B2
(45) Date of Patent: Mar. 6, 2012

(54) IMPEDANCE MONITORING FOR DETECTING PULMONARY EDEMA AND THORACIC CONGESTION

(75) Inventors: Andres Belalcazar, Saint Paul, MN (US); Robert Patterson, Minneapolis, MN (US); Rebecca Shult, Agoura Hills, CA (US)

(73) Assignee: Regents of the University of Minnesota, Saint Paul, MN (US)

( * ) Notice: Subject to any disclaimer, the term of this patent is extended or adjusted under 35 U.S.C. 154(b) by 575 days.

(21) Appl. No.: 11/936,357

(22) Filed: Nov. 7, 2007

(65) Prior Publication Data

US 2008/0125826 A1    May 29, 2008

Related U.S. Application Data

(63) Continuation of application No. 10/303,305, filed on Nov. 25, 2002, now Pat. No. 7,313,434.

(51) Int. Cl.
*A61B 5/05* (2006.01)
*A61B 5/02* (2006.01)
*A61B 5/08* (2006.01)

(52) U.S. Cl. .................. 600/547; 600/508; 600/529

(58) Field of Classification Search .................. 600/547; 607/9, 1, 17, 18, 19, 20, 24, 281
See application file for complete search history.

(56) References Cited

U.S. PATENT DOCUMENTS

| | | | |
|---|---|---|---|
| 3,340,867 A | 9/1967 | Kubicek et al. | |
| 4,817,634 A | 4/1989 | Holleman et al. | |
| 4,932,408 A | 6/1990 | Shaldach | |
| 5,036,849 A | 8/1991 | Hauck et al. | |
| 5,154,170 A | 10/1992 | Bennett et al. | |
| 5,284,136 A | 2/1994 | Hauck et al. | |
| 5,438,987 A | 8/1995 | Thacker et al. | |
| 5,501,702 A | 3/1996 | Plicchi et al. | |
| 5,556,421 A | 9/1996 | Prutchi et al. | |

(Continued)

FOREIGN PATENT DOCUMENTS

WO   WO2004045406   6/2004

OTHER PUBLICATIONS

Bocchiardo et al., "Biventricular Pacing Optimization Using Impedance Feasibility Study," Europace Supplements, 2002, 3:A39, Abstract No. 54/3.

(Continued)

*Primary Examiner* — Max Hindenburg
*Assistant Examiner* — Adam Eiseman
(74) *Attorney, Agent, or Firm* — Fish & Richardson P.C.

(57) ABSTRACT

An implantable medical device includes a housing for the implantable device that is sized for implantation in a chest region of a patient and includes a housing electrode. A left ventricular lead port is connectable to a proximal end of a lead having first and second insulated conductors that extend from the proximal end of the lead to corresponding first and second electrodes near a distal end of the lead. An electrical impedance measurement circuit is electrically connected to the left ventricular lead port and the housing electrode. The circuit may inject current between the first lead electrode and the housing electrode, and measure a voltage potential, created by the current injection, between the second lead electrode and the housing electrode. The ratio of the measured voltage to injected current may be used for assessing pulmonary edema. The lead electrodes may be located in a left ventricular coronary vein.

28 Claims, 12 Drawing Sheets

U.S. PATENT DOCUMENTS

| | | | |
|---|---|---|---|
| 5,814,076 | A | 9/1998 | Brownlee |
| 5,824,029 | A | 10/1998 | Weijand et al. |
| 5,876,353 | A | 3/1999 | Riff |
| 5,931,858 | A | 8/1999 | Kadhiresan et al. |
| 5,957,861 | A | 9/1999 | Combs et al. |
| 5,974,340 | A | 10/1999 | Kadhiresan |
| 6,070,100 | A | 5/2000 | Bakels et al. |
| 6,076,015 | A | 6/2000 | Hartley et al. |
| 6,104,949 | A | 8/2000 | Pitts Crick et al. |
| 6,161,042 | A | 12/2000 | Hartley et al. |
| 6,223,079 | B1 | 4/2001 | Bakels et al. |
| 6,269,264 | B1 | 7/2001 | Weyant et al. |
| 6,277,078 | B1 | 8/2001 | Porat et al. |
| 6,278,894 | B1 | 8/2001 | Salo et al. |
| 6,360,123 | B1 | 3/2002 | Kimchi et al. |
| 6,438,408 | B1 | 8/2002 | Mulligan et al. |
| 6,454,719 | B1 | 9/2002 | Greenhut |
| 6,473,640 | B1 | 10/2002 | Erlebacher |
| 6,512,949 | B1 | 1/2003 | Combs et al. |
| 6,595,927 | B2 | 7/2003 | Pitts-Crick et al. |
| 7,191,000 | B2 * | 3/2007 | Zhu et al. .................. 607/9 |
| 7,899,522 | B1 * | 3/2011 | Koh et al. ................. 600/513 |
| 7,907,998 | B2 * | 3/2011 | Arad (Abboud) ............ 600/547 |
| 7,917,194 | B1 * | 3/2011 | Reed et al. ................. 600/509 |
| 2001/0020138 | A1 | 9/2001 | Ishigooka et al. |
| 2002/0002389 | A1 | 1/2002 | Bradley et al. |
| 2002/0072686 | A1 | 6/2002 | Hoey et al. |
| 2002/0115939 | A1 | 8/2002 | Mulligan et al. |
| 2002/0123674 | A1 | 9/2002 | Plicchi et al. |
| 2002/0143368 | A1 | 10/2002 | Bakels et al. |
| 2002/0161310 | A1 | 10/2002 | Daum |
| 2003/0023184 | A1 | 1/2003 | Pitts-Crick et al. |
| 2003/0028221 | A1 | 2/2003 | Zhu et al. |
| 2003/0055461 | A1 * | 3/2003 | Girouard et al. .............. 607/17 |
| 2003/0078619 | A1 | 4/2003 | Bonnet et al. |
| 2003/0093125 | A1 | 5/2003 | Zhu et al. |
| 2003/0191503 | A1 * | 10/2003 | Zhu et al. .................. 607/17 |
| 2004/0049235 | A1 * | 3/2004 | Deno et al. .................. 607/9 |
| 2004/0102712 | A1 | 5/2004 | Belalcazar et al. |

OTHER PUBLICATIONS

Bronzino (ed.), "Chapter 73—Bioelectric Impedance Measurements," The Biomedical Engineering Handbook, Second Edition, vol. 1, 2000, A CRC Handbook Published in Cooperation with IEEE Press, pp. 73-1-73-8.

Cole et al., "Correlation of Impedance Minute Ventilation with Measured Minute Ventilation in a Rate Responsive Pacemaker," PACE, 2001, 24:989-993.

Duru et al., "Rate Responsive Pacing Using Transthoracic Impedance Minute Ventilation Sensors: A Multicenter Study on Calibration Stability," PACE, 2002, 25(12):1679-1684.

Hauck, "A Minute Ventilation Sensor Derived from Intra-Thoracic Electric Impedance as a Cardiac Pacemaker Rate Modulator," A Thesis Submitted to the Faculty of the Graduate School of the University of Minnesota, Department of Electrical Engineering, Jun. 1993, 148 pgs.

Nappholtz et al., "Electrode Configurations for a Respiratory Impedance Measurement Suitable for Rate Responsive Pacing," PACE, 1986, Part II, vol. 9, pp. 960-964.

Patterson, "Possible technique to measure ventricular volume using electrical impedance measurements with an oesophageal electrode," Med. & Biol. Eng. & Comput., 1987, 25:677-679.

Plicchi et al., "Monitoring Intrapulmonary Bioelectric Impedance During Active Volume Overloading," Europace Supplements, 2002, 3:A39, Abstract No. 54/6.

Simulation Data—relating to Left and Right Pectoral Can Table and Plots, Corrected Version Dec. 13, 2002, 2 pgs.

Van De Water et al., "Monitoring the Chest with Impedance," Chest, 1973, 64(5):597-603.

Wang et al., "Feasibility of Monitoring Thoracic Congestion with Impedance Measured from an ICD Lead System in a Chronic Heart Failure Dog Model," PACE, NASPE Abstracts, 2000, Part II, vol. 23, No. 4, p. 612, Abstract No. 237.

Wang et al., "Feasibility of Predicting CHF Hospitalization Using Pacemaker-Based Impedance Sensor in CHF Patients," J. Cardiac Failure, 2002, 8(4, Suppl.):S81, Abstract No. 297.

Yu et al., "Early Warning of CHF Hospitalization by Intra-Thoracic Impedance Measurement in CHF Patients with Pacemakers," PACE, NASPE Abstracts, 2002, Part II, vol. 25, No. 4, p. 527, Abstract No. 19.

Malmivuo J. et al.; "Impedance plethysmography", *Bioelectromagnetism: Principles and Applicants of Bioelectic and Biomagnetic Fileds*, Oxford University Press, GB, Nov. 1, 1995, pp. 405-407.

Notification of Transmittal of the International Search Report and The Written Opinion of the International Searching Authority, dated Oct. 19, 2007, International Appln No. PCT/US06/05060.

European Supplementary Search Report, dated Sep. 9, 2009; EP Appln No. 06 73 4952.

* cited by examiner

Simulation Results: Tripolar Configuration, Left Pectoral Can

| Systole | Normal (Ohms) | Edema (Ohms) | Delta Z (Ohms) | % chg | Sensitivity (Milliohm/Ohm-cm) |
|---|---|---|---|---|---|
| RV Coil | 48.70 | 41.13 | -7.57 | 15.6% | 7.21 |
| RV | 69.72 | 61.92 | -7.80 | 11.2% | 7.43 |
| RA | 24.72 | 20.42 | -4.30 | 17.4% | 4.10 |
| LVCV | 84.64 | 56.76 | -27.87 | 32.9% | 26.55 |
| Diastole | | | | | |
| RV Coil | 54.31 | 46.73 | -7.58 | 14.0% | 7.22 |
| RV | 75.97 | 68.29 | -7.68 | 10.1% | 7.32 |
| RA | 23.11 | 18.83 | -4.28 | 18.5% | 4.08 |
| LVCV | 60.35 | 45.98 | -14.37 | 23.8% | 13.69 |

Sensitivity to Simulated Lung Edema
Tripolar Configuration - Left Pectoral Can

Simulation Results: Tripolar Configuration, Right Pectoral Can

| Systole | Normal (Ohms) | Edema (Ohms) | Delta Z (Ohms) | % chg | Sensitivity (Milliohm/ Ohm-cm) |
|---|---|---|---|---|---|
| RV Coil | 19.47 | 16.47 | -3.00 | 15.4% | 2.86 |
| RV | 27.26 | 24.17 | -3.09 | 11.4% | 2.95 |
| RA | 24.33 | 19.44 | -4.89 | 20.1% | 4.66 |
| LVCV | 36.76 | 24.43 | -12.33 | 33.5% | 11.74 |
| Diastole | | | | | |
| RV Coil | 21.05 | 18.23 | -2.82 | 13.4% | 2.69 |
| RV | 28.99 | 26.16 | -2.84 | 9.8% | 2.70 |
| RA | 22.40 | 17.48 | -4.92 | 22.0% | 4.69 |
| LVCV | 26.18 | 19.82 | -6.37 | 24.3% | 6.06 |

IMPEDANCE MONITORING FOR DETECTING PULMONARY EDEMA AND THORACIC CONGESTION

TECHNICAL FIELD

The description relates to impedance monitoring in a living being for the detection of pulmonary edema and thoracic congestion.

BACKGROUND

Pulmonary edema is a serious medical condition caused by an excess accumulation of fluid within a patient's lungs. Pulmonary edema can be an indicator of cardiac-related diseases, such as congestive heart failure. Good management of pulmonary edema is desirable because it may allow timely therapeutic interventions, and avoid hospitalization and its costs.

It is possible to detect fluid in the lungs by making an electrical impedance measurement across the lungs. The more fluid there is in the lungs, the lower the impedance. One known way this may be done is by using an implantable medical device such as a pacemaker or defibrillator implanted in the chest area of the patient. An electrical impedance measurement is conventionally made between right ventricular chamber electrodes connected to the implanted device, and another electrode at the implanted device itself; thus, the impedance measurement samples thoracic tissues, including the lungs. This configuration may also be used to measure impedance for determining a patient's respiration rate, which may subsequently be used to aid in the regulation and issuance of pacing stimuli to the heart. For instance, a patient whose respiration rate increases due to exercise, for example, may require pacing stimuli to be delivered at a faster rate.

SUMMARY

The invention provides improved techniques for measuring electrical impedance across lung tissue so that pulmonary edema, or its onset, may be detected more accurately and sensitively.

In one general aspect, an implantable medical device includes a housing for the implantable device that is sized for implantation in a chest region of a patient and includes a housing electrode. A left ventricular lead port is connectable to a proximal end of a lead. The lead has first and second insulated conductors that extend from the proximal end of the lead to corresponding first and second electrodes near a distal end of the lead. The device further includes an electrical impedance measurement circuit that is electrically connected to the left ventricular lead port and to the housing electrode. The electrical impedance measurement circuit injects current between the first lead electrode and the housing electrode. A voltage potential, created by the current injection, is measured by the electrical impedance measurement circuit between the second lead electrode and the housing electrode.

Implementations may include one or more of the following. The lead electrodes may be configured for positioning within a left ventricular coronary vein. Alternatively, the lead electrodes may be epicardial electrodes, which may be configured to be sutured to a wall of a left ventricle. The housing electrode may be a can electrode, or, alternatively, a header electrode. The current injection and voltage potential measurement may be done to make an electrical impedance measurement. In some implementations, the impedance measurement circuit measures electrical impedance at a moment of end-systole and end-expiration, at a specified heart rate range, or at a specified posture. The electrical impedance measurement may be used to assess pulmonary edema or thoracic congestion. A telemetry circuit may be included for transmitting electrical impedance measurements to an external receiving station.

In another aspect, the device includes, in addition to the housing and left ventricular lead port as described above, a right atrial lead port. The right atrial lead port is connectable to a proximal end of a second lead having first and second insulated conductors that extend from the proximal end of the second lead to corresponding third and fourth electrodes positioned near a distal end of the second lead. The electrical impedance measurement circuit is electrically connected to the right atrial lead port, and may inject a second current between the third electrode and the housing electrode. A second voltage potential, created by the second current injection, may be measured by the electrical impedance circuit between the fourth electrode and the housing electrode.

Implementations may also include one or more of the following. In addition to measuring a first electrical impedance as discussed above, the current injection and voltage measurement between the right atrial lead electrodes and the housing electrode is done to make a second electrical impedance measurement. In some implementations, the impedance measurement circuit may measure the second electrical impedance at a moment of end-diastole and end-expiration. A circuit may calculate a weighted combination of the first and second electrical impedances.

In another aspect, the invention provides for a method of monitoring pulmonary edema or thoracic congestion in a human being. An electrical current is injected between a first electrode located in a coronary vein of a left ventricle and a housing of a medical device implanted in a chest region. A voltage potential, created by the current injection, is measured between a second electrode located in the coronary vein of the left ventricle and the medical device housing. Then, an impedance value may be calculated by taking a ratio of the measured voltage potential to the injected current. The impedance value may be used to assess pulmonary edema or thoracic congestion.

In another aspect, the invention provides for a method of monitoring pulmonary edema or thoracic congestion in a human being by obtaining the first impedance value as described above, and injecting a second electrical current between a third electrode located in a right atrium and the medical device housing. A second voltage potential, created by the second current injection, is measured between a fourth electrode located in the right atrium and the medical device housing. A second impedance value may then be calculated by taking a ratio of the measured second voltage potential to the injected second current. In some implementations, a weighted combination of the first and second impedance values is used to assess pulmonary edema or thoracic congestion.

In another aspect, the invention provides for a method of determining electrical impedance in a human being. The method includes measuring an electrical impedance between a housing of a medical device implanted in a chest region and electrodes located in a coronary vein of a left ventricle, and determining a degree of pulmonary edema in the human being based on the measured electrical impedance. The method further includes receiving orientation information indicating a position of the human being from a posture sensor, and adjusting a relationship between the electrical impedance and the degree of pulmonary edema based on the orientation information.

Advantages of the invention may include one or more of the following. A new level of lung impedance measurement sensitivity is possible using aspects of the invention. For example, impedance measurements will have better sensitivity compared to previously known techniques. Impedance measurements made with an implantable device in a chest region, with the device having an impedance circuit connected to a left ventricle port and housing, have been simulated and shown to provide about a threefold increase in sensitivity versus a conventional device having the impedance circuit connected to the right ventricular port. The novel left ventricle port configuration exploits the epicardial location of left ventricular electrodes. The novel right atrium port configuration exploits the close location of the atrium to the lung, and the thin walls of the atrium. As such, better pulmonary edema or thoracic congestion assessments may be made, and serious conditions may be detected earlier. In addition, a weighted combination of the discussed measured impedances may provide a more global and specific lung impedance assessment, and thus permit a better assessment of pulmonary edema or thoracic congestion.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
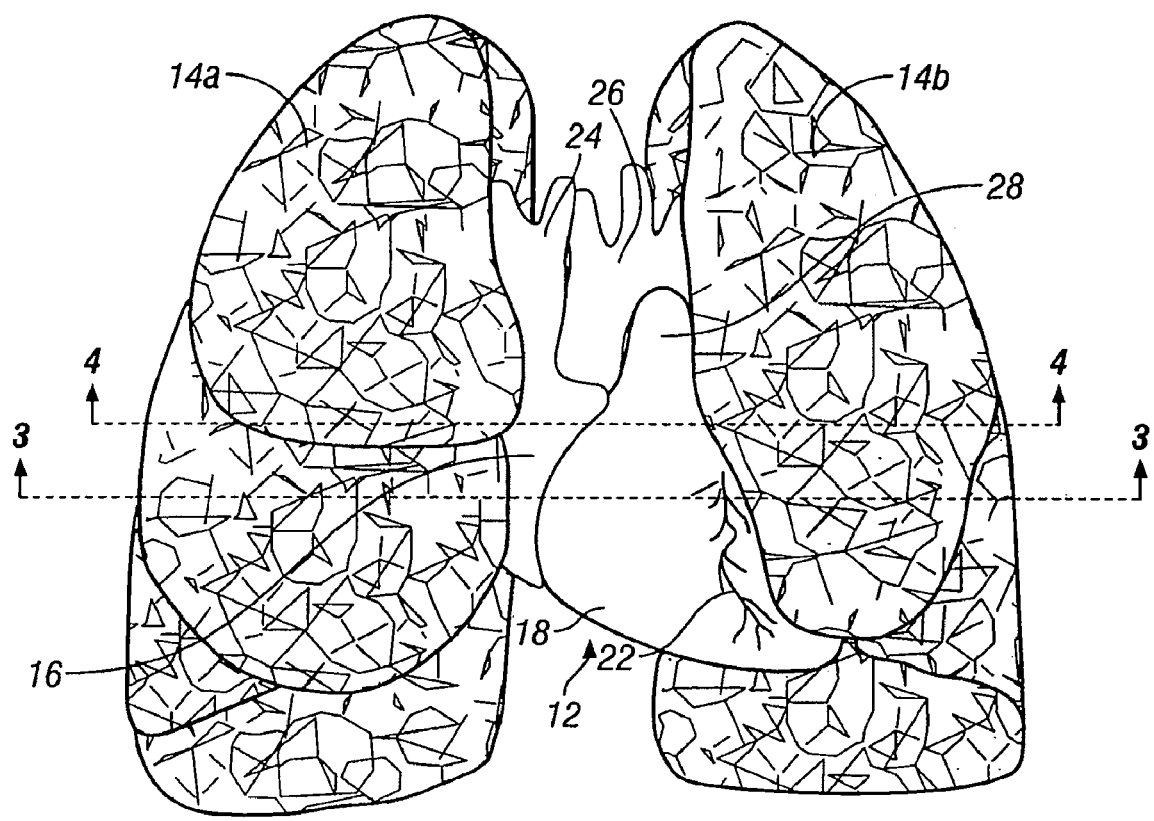
FIG. 1 is a perspective diagram of a human heart and lungs.

Before discussing the medical device used to detect pulmonary edema or thoracic congestion, it will be helpful to discuss first the relative positioning of a human heart and lungs, and the phases of a cardiac cycle. FIG. 1 is a front view of a human heart 12 positioned between a right lung 14a and a left lung 14b.

A superior vena cava 24 receives deoxygenated blood from a body's upper extremities and thorax, and empties the blood into a right atrial chamber 16, referred to as the right atrium.

A left atrial chamber (left atrium, not shown in FIG. 1) conversely receives oxygenated blood from the lungs 14. The atria (right atrium 16 and left atrium) then contract and force blood into a right ventricular chamber 18 (right ventricle), and left ventricular chamber (left ventricle, covered by the left lung 14b in FIG. 1), respectively. After this atrial contraction, the cardiac cycle reaches the end of diastole, with the ventricles dilated and filled with blood. The right ventricle 18 and left ventricle serve as blood pumps to pump blood away from the heart 12. The right ventricle 18 pumps deoxygenated blood to the lungs 14 through a pulmonary artery 28. Within the lungs 14, the blood becomes re-oxygenated and is then moved to the left atrium, as discussed above. The left ventricle, having received oxygenated blood from the lungs 14 through the left atrium, pumps the oxygenated blood to the body through an aorta 26, a large artery leaving the left ventricle. This second part of the cardiac cycle may be referred to as systole, because the ventricles contract as the blood is pumped therefrom.

In FIG. 1, a section of the aorta 26 known as the aortic arch is shown. An inter-ventricular vein 22, which runs substantially vertically in FIG. 1, marks a division between the right ventricle 18 and left ventricle. As seen in FIG. 1, the lungs 14 are close to the heart 12, the closest portions being the left ventricle and right atrium 16. The right ventricle 18, in contrast, is located away from the lungs 14, approximately between the right lung 14a and left lung 14b on the anterior side.

Figure 2:
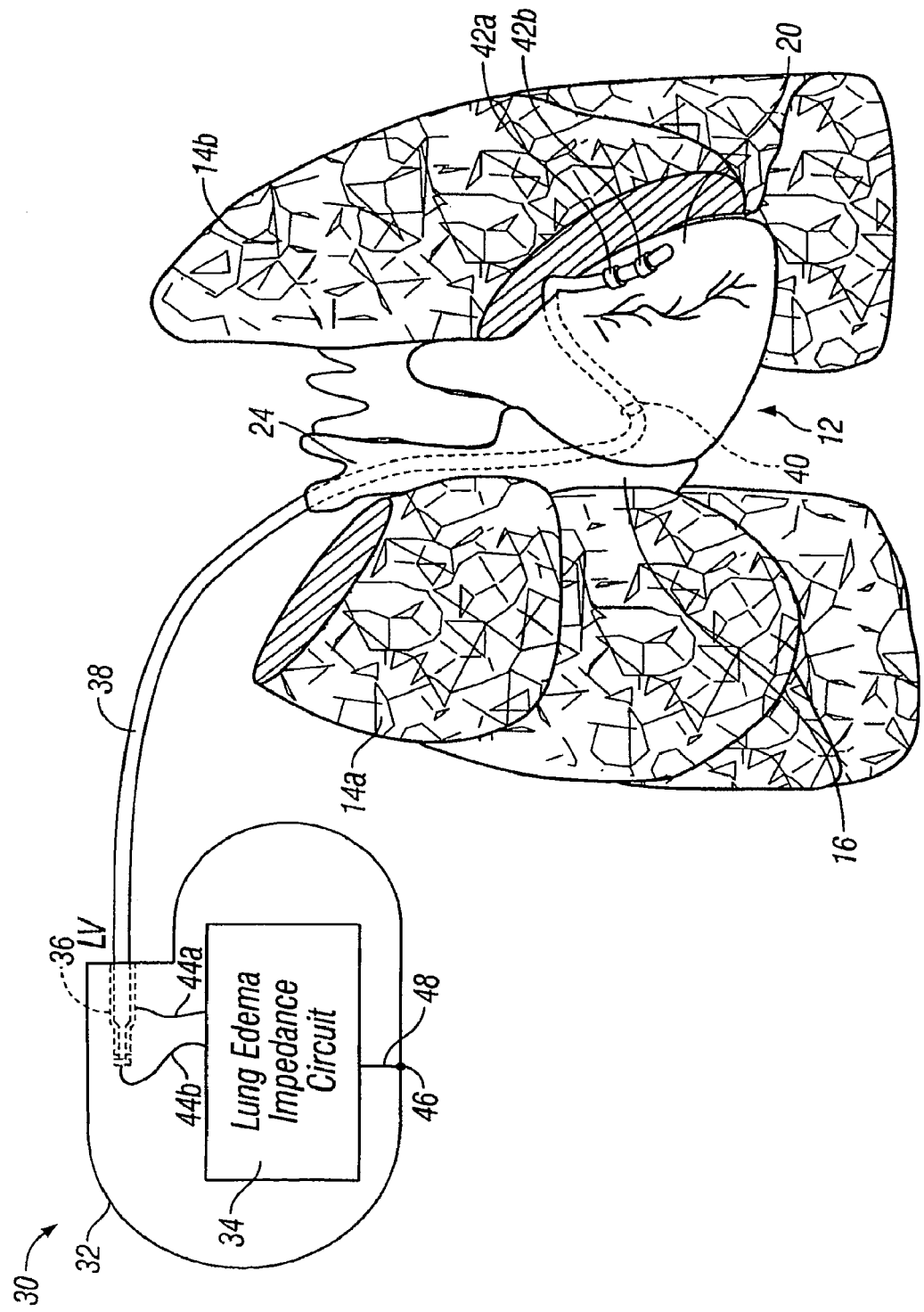
FIG. 2 is a diagram of an implantable device in accordance with an embodiment of the invention and the heart and lungs from FIG. 1.

Referring now to FIG. 2, an illustrative view of the heart and lungs from FIG. 1 and an implantable device 30 is shown. The implantable device 30 includes a housing 32 that houses a lung edema impedance circuit 34. The lung edema impedance circuit 34 may measure lung impedance and assess pulmonary edema levels. The device 30 includes a left ventricular port 36 for attaching a left ventricular cardiac lead 38. In FIG. 2, the lead 38 is attached to the left ventricular port 36. The lead 38 may then be introduced into the venous system, down the superior vena cava 24, into the right atrium 16, into a coronary sinus through an orifice 40 (the Os of the coronary sinus), and then further into coronary veins (not shown in FIG. 2), which run epicardially over the left ventricle 20 (visible in FIG. 2 because portions of the lungs 14 have been removed for display purposes).

The lead 38 has two electrodes 42a, 42b that are electrically connected to conductors (not shown) that run through the lead 38. The conductors connect to conducting wires 44a, 44b, respectively, within the device 30 when the lead 38 is attached to the port 36, thereby establishing electrical connections between the lung edema impedance circuit 34 and the electrodes 42a, 42b. Electrode 42a may be referred to as a proximal electrode, and electrode 42b may be referred to as a distal electrode because of their relative positions on lead 38. Although electrodes 42a and 42b are shown as ring electrodes, either may alternatively be a tip electrode, or may alternatively be located elsewhere along lead 38. While a bipolar lead 38 is shown in FIG. 2, lead 38 may optionally include additional or fewer electrodes, and may follow a different path through the heart 12 from that shown in FIG. 2.

A can electrode 46 on an exterior surface of the device housing 32 is electrically connected to the lung edema impedance circuit 34 through a wire 48 and completes a tripolar electrode configuration whereby an electrical current may be injected between a lead electrode (the distal electrode 42b, for example) and the can electrode 46, and a voltage may be measured between the other lead electrode (42a) and the can electrode 46. As opposed to using a can electrode 46, a header electrode could alternatively be used. The header electrode may be a conductor located on an exterior surface of a header of the device 30. As seen in FIGS. 1-2, lead placement near the left ventricle 20 provides a suitable location for measuring lung impedance due to the proximity of the left lung 14b, compared to an anatomically less-desirable right ventricle placement, as is conventional. This provides a more sensitive impedance measurement so that a better edema assessment may be made.

Device 30 may optionally include a second can electrode or a header electrode to facilitate a tetrapolar electrode configuration. A bipolar configuration is also possible. Wires 44a, 44b, and 48 may alternatively be traces on a printed circuit board, for example, or any other conventional electrical connection elements. Can electrode 46 may comprise a substantial portion of an external surface of housing 32, such that the interface impedance of the can electrode 46 is relatively low. Alternatively, lead 38 may bifurcate distally into two sub-leads and terminate in two epicardial electrodes, which may be sutured to a wall of the left ventricle 20. The epicardial electrodes may comprise conductive surfaces facing the left lung 14b, and may function in a similar manner to the lead electrodes 42 described above. The implantable device 30 may be, for example, a pacemaker or defibrillator (or a combination of both), or an infusion pump, and should be sized for implantation in a chest region of a patient.

Figure 3:
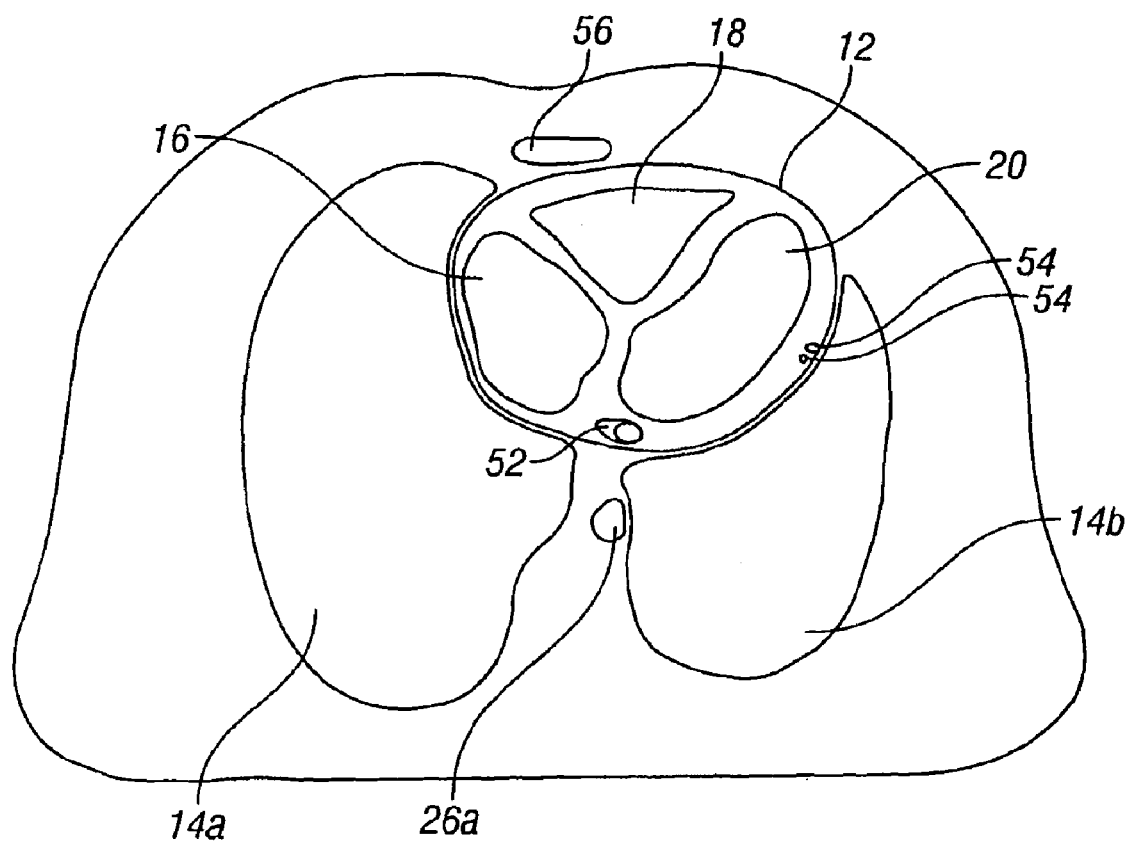
FIGS. 3-4 are cross-sectional views of a human thorax through the heart and lungs, the cross-sections being indicated in FIG. 1.

FIG. 3 shows an anatomical cross-section of a human thorax including the heart 12 and lungs 14 through a transverse plane that shows the proximity of the left ventricle 20 to the left lung 14b. Specifically, FIG. 3 shows coronary veins 54 that are the location for the left ventricular cardiac lead 38 (FIG. 2) after passing through the coronary sinus 52. Similarly, the right atrium 16 has a proximal location to the right lung 14a, while the right ventricle 18 is not close to either lung 14a,14b. A descending portion 26a of the aorta 26 (referred to as the descending aorta), and a sternum 56 are also shown.

Figure 4:
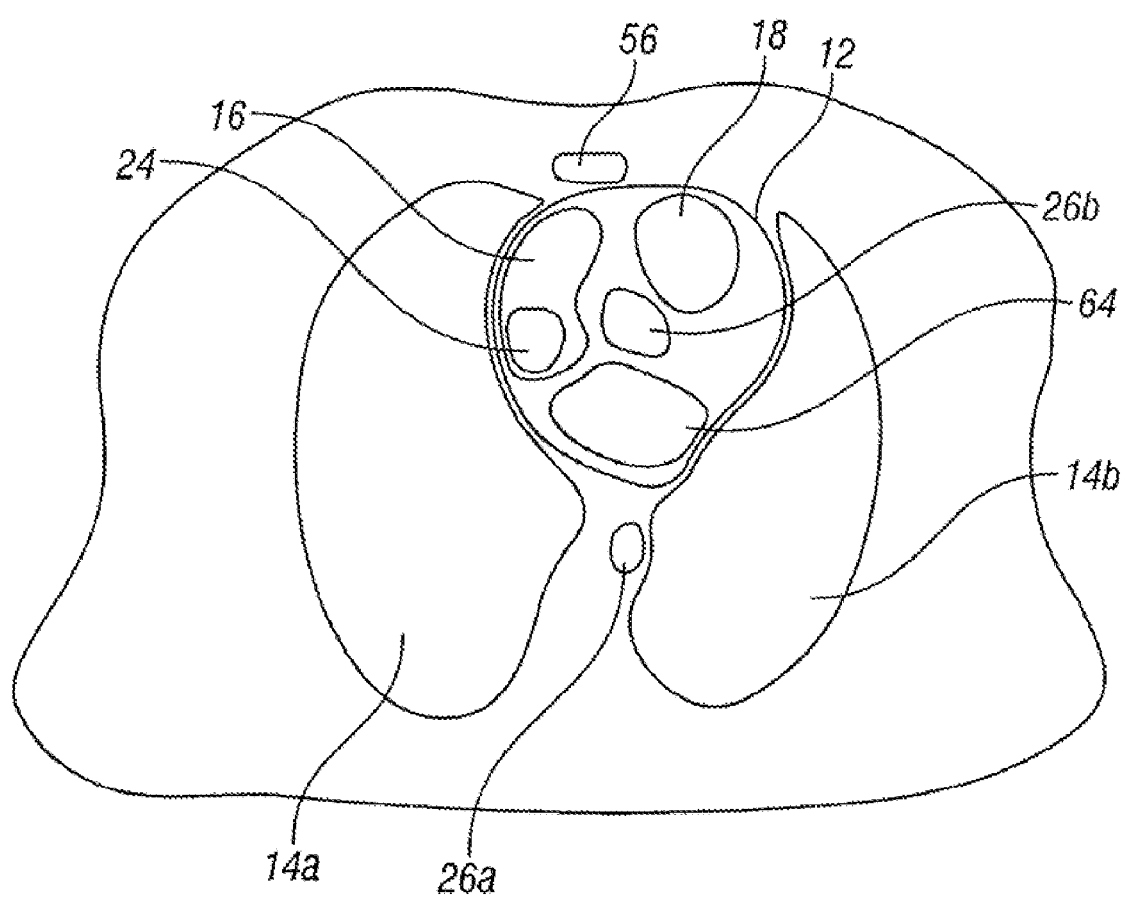

FIG. 4 shows another anatomical cross-section of a human thorax through a superior or higher transverse plane than that shown in FIG. 3. In FIG. 4, the superior vena cava 24 is shown entering the right atrium 16. Similar to the left ventricular coronary vein location 54 (FIG. 3), the right atrium 16 provides a useful location (discussed later) for making lung impedance measurements because of the proximity of the right lung 14a. Similar to the view of FIG. 3, FIG. 4 shows that the superior portion of right ventricle 18 is not close to the lungs 14. FIG. 4 shows both the descending aorta 26a, and also an ascending portion 26b (referred to as the ascending aorta) of the aorta 26. The left atrium 64 is shown, along with the sternum 56.

Figure 5:
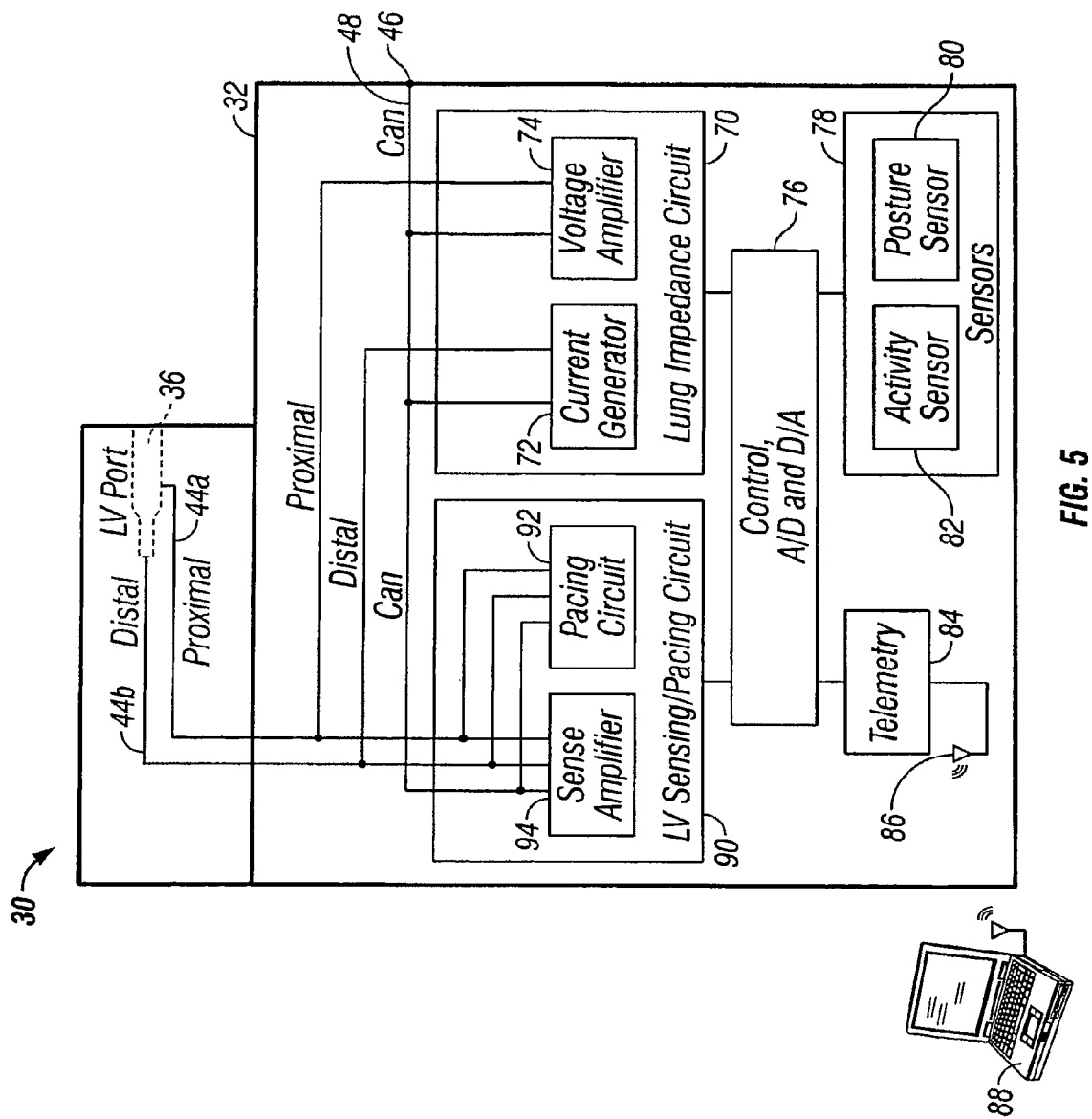
FIG. 5 is a more detailed view of an embodiment of the device shown in FIG. 2, showing a block diagram of circuitry within the device and an external device.

FIG. 5 shows a block diagram circuit representation of the implantable device 30 from FIG. 2. Device 30 includes circuits for measuring impedance and making pulmonary edema assessments, and communication circuits for interfacing with external devices. A lung impedance circuit 70 includes a current generator 72, which may inject an electrical current between the can electrode 46 and the distal left ventricular coronary vein electrode 42b (FIG. 2) over wires 48,44b, and conductors through lead 38 (not shown in FIG. 5). Thus, part of the current flows across the left lung 14b, which is situated very near the lead electrode 42b. The injection current may be an alternating current (AC) to avoid undesirable polarization and electrolytic degradation effects at the electrodes 46,42b, and should be of such magnitude, frequency, and duration that it does not cause cardiac stimulation. In one implementation, the AC current may have a frequency of about 50 KHz-100 KHz. Examples of possible current waveforms include sine waves and biphasic pulses (symmetric or otherwise).

The injection current between electrodes 42b and 46 (see FIG. 2) creates an electric field in the body of a patient. Thus, a voltage potential appears between electrodes 42a and 46. A voltage amplifier 74 may then measure this voltage between electrodes 42a and 46 over wires 48,44a, and conductors through lead 38. The voltage amplifier may, for example, be a signal-conditioning unit to measure the voltage, and may optionally include a demodulator. Alternatively, the roles of the proximal and distal electrodes 42a,42b, could be reversed, with the appropriate wiring modifications. As noted earlier, tetrapolar and bipolar configurations are possible alternative measurement configurations to the tripolar configuration described here.

A control block 76 receives or contains information on the magnitudes of both the injected current and the resulting measured voltage. Analog-to-digital (A/D) converters may be used to translate the information. A processing unit (not shown) such as a microprocessor, microcontroller, or digital signal processor within the control block 76 may then use the current and voltage information to calculate impedance by dividing voltage by current. As body tissue fluid levels increase, the tissue impedance decreases. Thus, the impedance ratio may be used to assess pulmonary edema, and a degree of pulmonary edema may be determined for the patient. An algorithm describing the edema value determination will be discussed later.

The control block 76, as is conventional, may additionally include read-only memory (ROM), random-access memory (RAM), flash memory, EEPROM memory, and the like, which may store instructions that may be executed by the processing unit, as well as digital-to analog (D/A) converters, timers, counters, filters, switches, etc. (not shown). Impedance measurements and edema values may also be stored in memory. These control block components may be integrated within a single device, such as an application specific integrated circuit (ASIC), or alternatively may be separate devices. Appropriate busses (not shown) allow communication between components within control block 76.

Information from a sensor block 78 may be used to adjust the relationship between the measured impedance and the degree of edema. A posture sensor 80 may provide patient orientation information to the control block 76, allowing posture compensation to be included in the assessment of edema. Because organs and excess fluid in the thorax and lungs 14 shifts with posture changes due to gravity, measured impedance may vary as a patient assumes different positions. For example, when a patient lies on his/her right side, fluid and tissues in the left lung 14b may gravitate towards the mediastinum near the left ventricular coronary vein electrodes 42, resulting in lower measured impedance. Thus, based on posture sensor information, the relationship between the impedance measurement and the degree of edema may be adjusted to compensate. Similarly, that relationship may be inversely adjusted for a patient lying on his/her left side. Several types of posture sensors could be used, including mercury switches, DC-accelerometers, or other piezoelectric devices.

An activity sensor 82, conventionally used to aid in pacing applications, may also provide information to the control block 76. By using these compensation schemes, edema interpretation errors caused by postural fluid shifts within a patient may be avoided. Either sensor 80, 82 may optionally be excluded from the implantable device 30.

A telemetry block 84 may communicate wirelessly using radio frequency (RF) transmissions over an antenna 86 with a similarly wirelessly equipped monitoring unit 88. Monitoring unit 88 may be a computer (custom programmer, desktop, laptop, handheld, etc.), a telemedicine home station, a wearable device such as a wristwatch, or any other appropriate device, and may be used to program the implantable device 30, or to retrieve information, such as impedance measurements and edema values. A left ventricular sensing/pacing circuit 90 includes a pacing circuit 92 and a sense amplifier 94 and is used to sense and/or stimulate (pace) left ventricular cardiac events. The generic lung edema impedance circuit 34 (FIG. 2) is not explicitly shown in FIG. 5, but would include several of the FIG. 5 blocks, or portions thereof. Conventional elements which may further be included in device 30 but are not shown include battery or power supply blocks, defibrillation circuits, and circuits for a right ventricular port.

Figure 6:
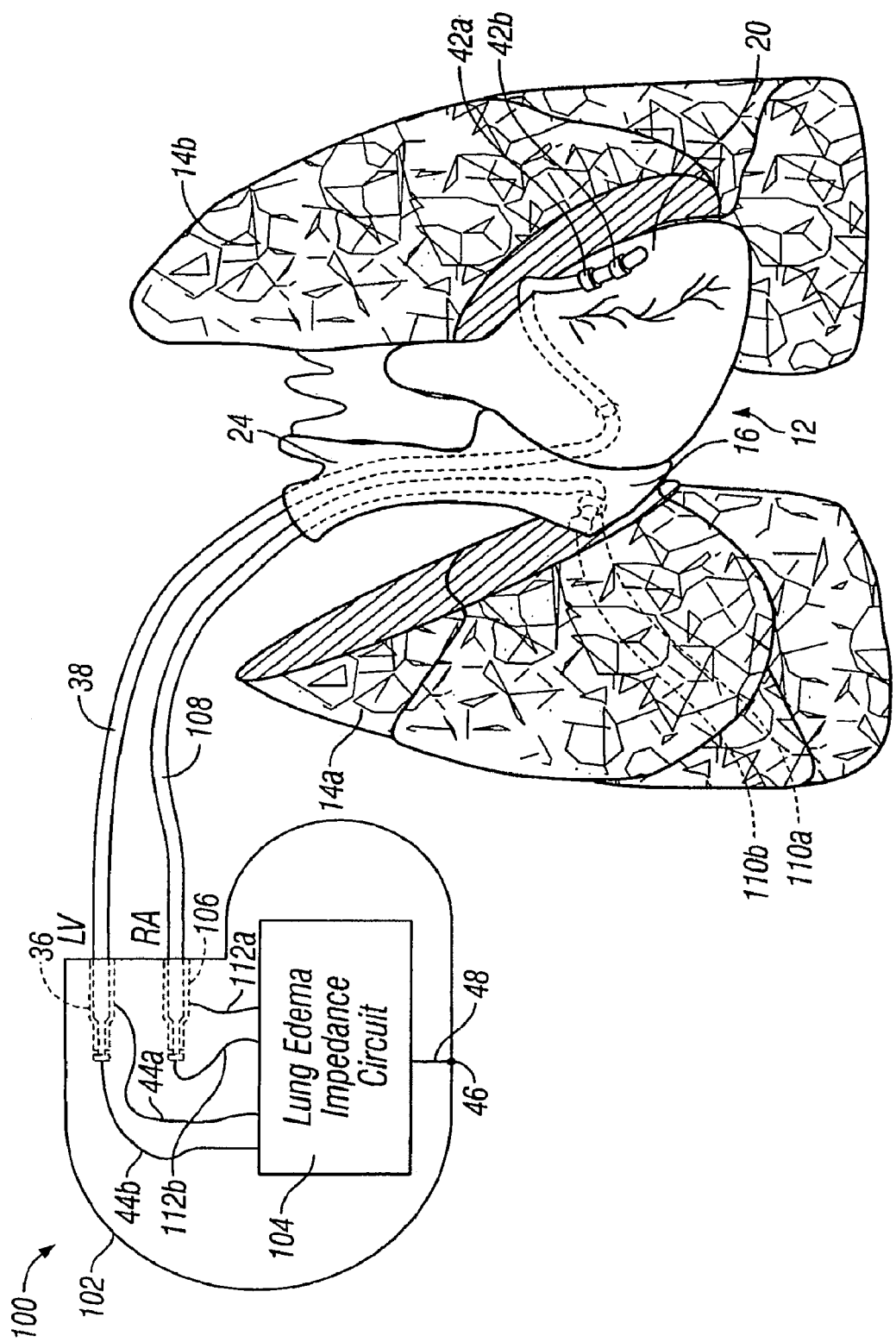
FIG. 6 is a diagram of an implantable device in accordance with another embodiment of the invention and the heart and lungs from FIG. 1.

FIG. 6 depicts an alternate embodiment showing the heart and lungs from FIG. 1 and another implantable device 100. The implantable device 100 includes a housing 102 that houses a lung edema impedance circuit 104, and includes a left ventricular port 36 for attaching a left ventricular cardiac lead 38, and a right atrial port 106 for attaching a right atrial cardiac lead 108. The right atrial lead 108 may then be introduced into the venous system, down the superior vena cava 24, and into the right atrium 16. The right atrial lead 108 has proximal and distal electrodes 110a, 110b that are electrically connected to conductors (not shown) that run through the right atrial lead 108. The conductors connect to conducting wires 112a, 112b, respectively, within the device 100 when the right atrial lead 108 is attached to the right atrial port 106, establishing electrical connections between the lung edema impedance circuit 104 and the right atrial electrodes 110a, 110b. Left ventricular lead 38 is located in coronary veins 54 (FIG. 3) of the left ventricle 20, as described above in the FIG. 2 discussion. Similar to the left ventricular lead 38, right atrial lead 108 may have additional or fewer electrodes, and may alternatively use a tip electrode, for example.

The FIG. 6 arrangement facilitates lung impedance measurements from both the right atrium 16, and a coronary vein 54 (FIG. 3) of the left ventricle 20. As such, a more global measurement of lung impedance, and hence a more global pulmonary edema assessment, may be obtained by using a weighted combination of the two impedance measurements. The weighted combination retains a high degree of specificity since each lead is anatomically located near the lungs 14. Furthermore, the combination may allow for a subtraction of common signal contributions from the heart and great vessels thereof, thereby allowing an even more lung-specific measurement.

Figure 7:
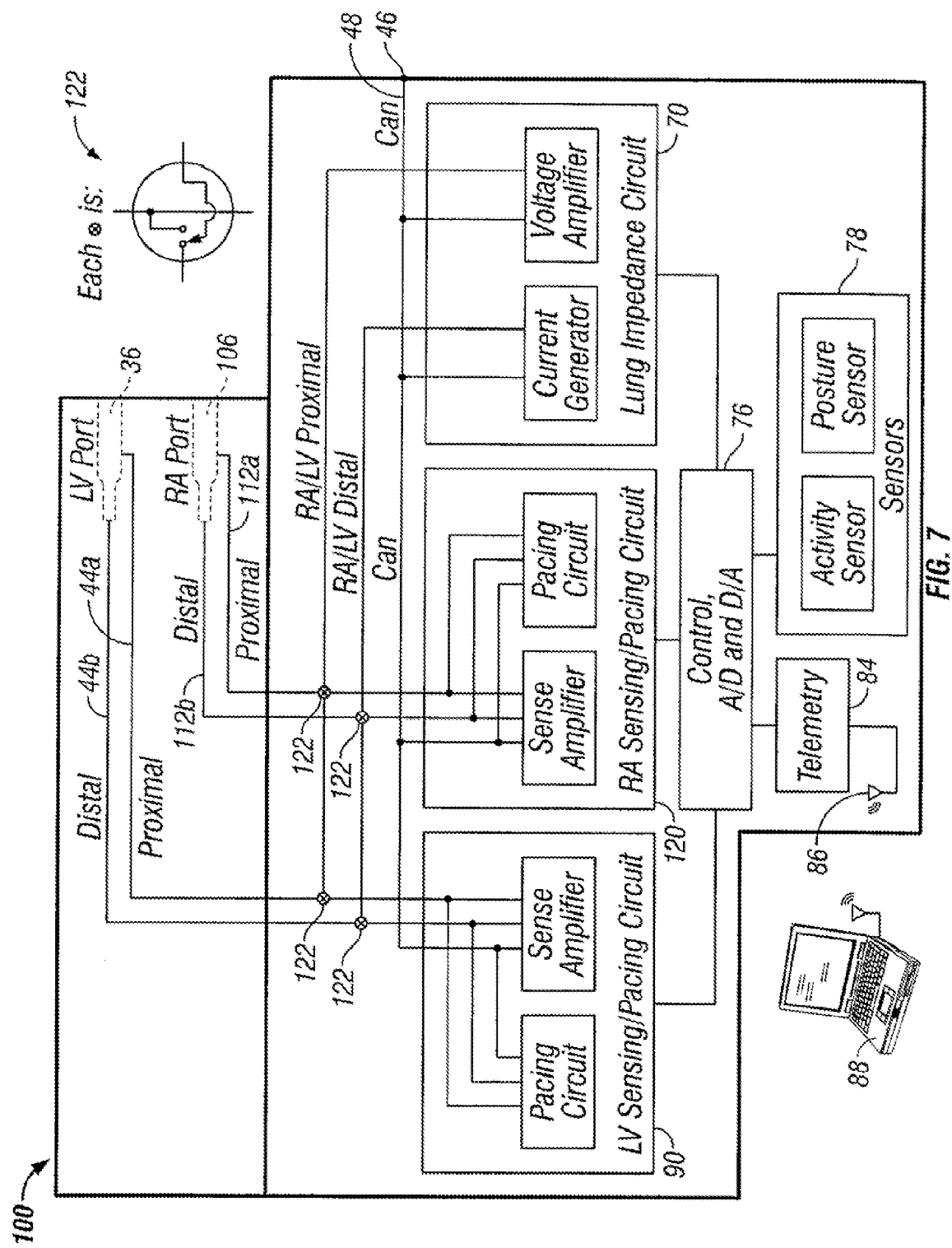
FIG. 7 is a more detailed view of an embodiment of the device shown in FIG. 6, showing a block diagram of circuitry within the device, an external device, and a switch.

FIG. 7 shows a block diagram circuit representation of the implantable device 100 from FIG. 6. FIG. 7 is similar to FIG. 5, with the addition of a right atrial sensing/pacing circuit 120 for sensing and/or stimulating right atrial cardiac events, and the addition of the right atrial port 106. An implementation may use a single lung impedance circuit 70 and switch connections in succession using switches 122 to obtain the right atrial and left ventricular impedance measurements. An exploded view of switch 122 is shown in the upper right corner of FIG. 7. Switches 122 may be controlled by control unit 76 (details not shown in FIG. 7).

To show that increased lung impedance measurement sensitivity is possible using embodiments of the invention, simulations were conducted using a computer modeling technique. A three-dimensional computer model that divides a human thorax into many small volumes, each corresponding to body tissue, was used to simulate lung impedance under normal and pulmonary edema conditions. Each small tissue volume is assigned an appropriate electrical resistivity (e.g. blood=150 ohms-cm, normal lung=1400 ohms-cm, muscle=400 ohms-cm, etc.) according to published tables. Electrodes may then be placed at various locations in the model, and current may be injected. The computer then calculates the resulting voltage potentials at each of the volumes using electric field equations. The results can be used to compute impedance by dividing the measured potentials by the injected current.

Figure 8:
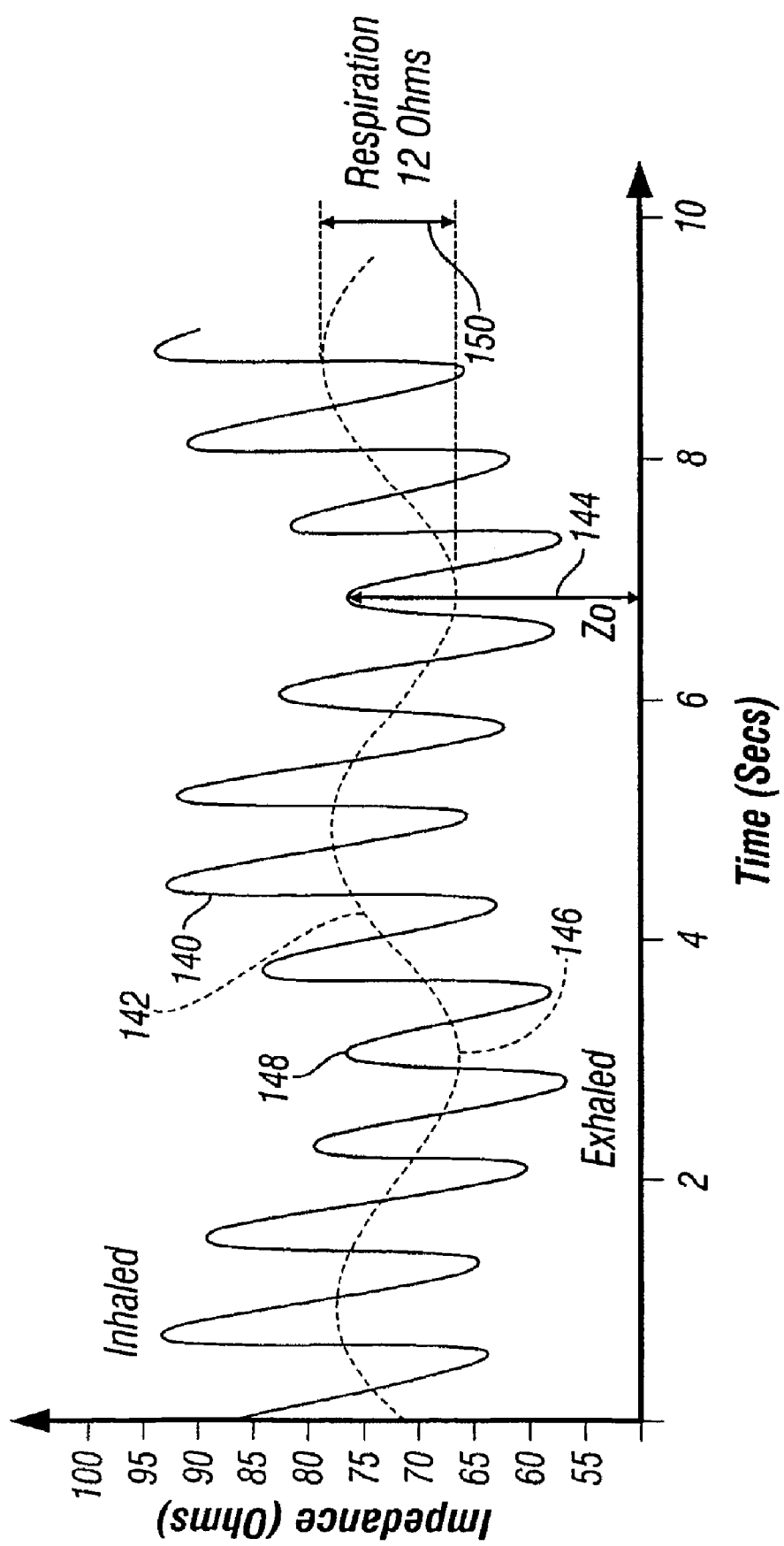
FIGS. 8-9 are impedance versus time waveforms.
Figure 9:
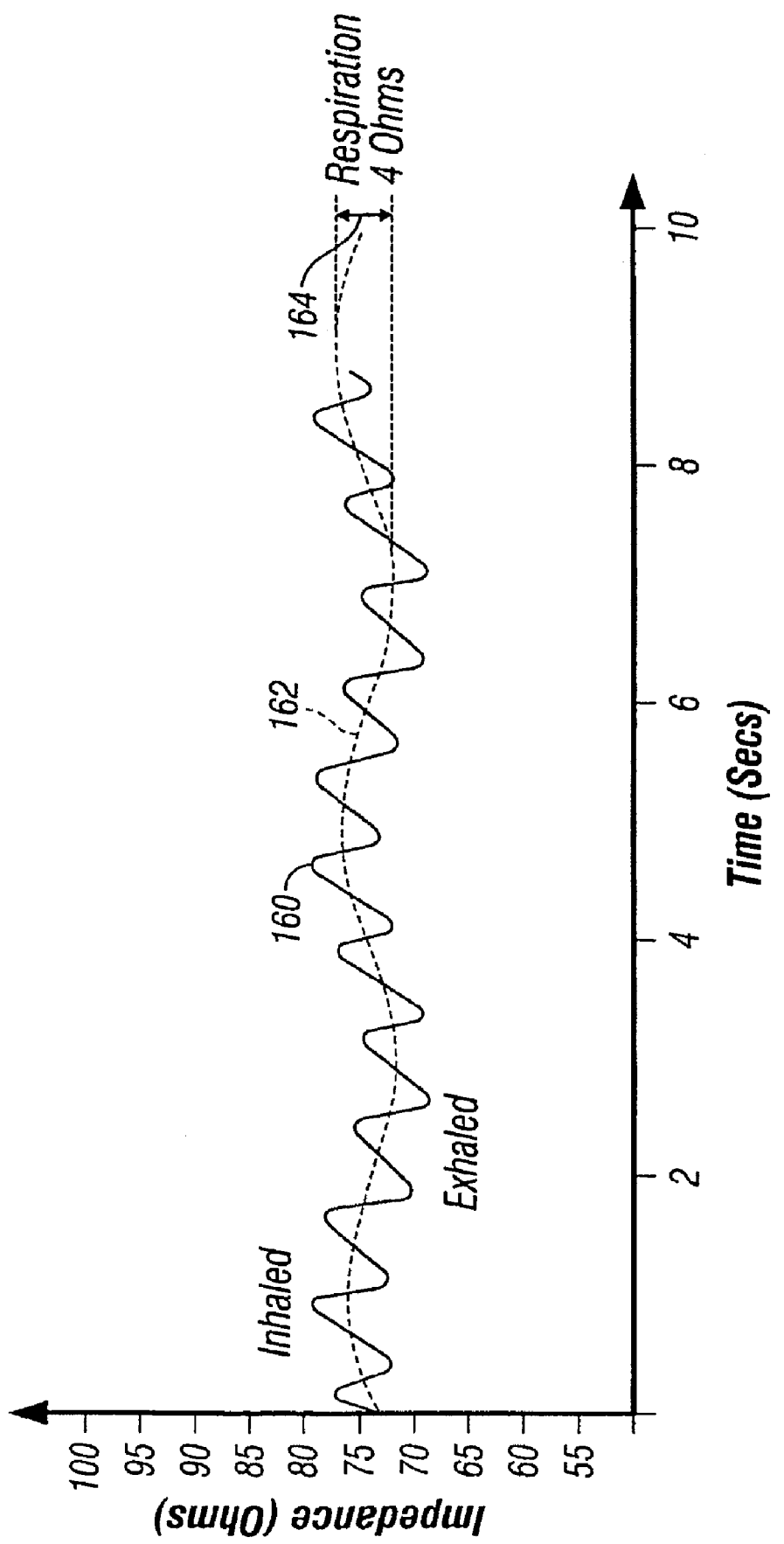

FIGS. 8 and 9 show impedance versus time computer simulation result waveforms using the model discussed above. FIGS. 8 and 9 correspond to a tripolar electrode measurement configuration with a left pectoral device implant location. FIG. 8 shows an impedance waveform 140 corresponding to a left ventricular coronary vein location for current injection and impedance measurement (e.g., as in FIG. 2), while FIG. 9 shows an impedance waveform 160 corresponding to a conventional right ventricular location for current injection and impedance measurement. The waveforms 140,160 are plotted to the same scale, and each corresponds to an adult with a heart rate of 80 beats per minute, a respiration rate of 15 breaths per minute, and a tidal volume of 2 liters.

Examining the waveforms 140,160, it can be noticed that in each case a slow oscillation component 142,162 at about 0.25 Hz, and a faster oscillation component at about 1.33 Hz are present. The former is due to breathing and may be referred to as a respiration component; the latter is due to the heartbeat and may be referred to as a cardiac component. As a patient inhales, impedance increases; as a patient exhales, impedance decreases. Furthermore, as the ventricles of the heart contract (systole), impedance increases at the left ventricular coronary vein measurement location.

Referring again to FIG. 8, impedance waveform 140 has a base impedance DC component Zo 144, (approximately 75 ohms in the simulation), which may be used to assess the state of edema in a patient. Zo 144 is at end-systole and end-expiration (that is, at a trough 146 of respiration component 142, and at a peak 148 of the cardiac component). It will be explained later that this measurement moment maximizes sensitivity, yielding better edema assessment results. The respiration component 142 may be used for determining respiration rate and depth, as in adaptive rate pacing applications. The FIG. 8 left ventricular coronary vein location respiration component 142 has a magnitude 150 of 12 ohms. Referring now to FIG. 9, the right ventricular location AC component 162 of impedance waveform 160 has a magnitude 164 of 4 ohms. Thus, the simulations show that the left ventricular coronary vein location is three times more sensitive to lung impedance variations than the conventional right ventricular location (12 ohms vs. 4 ohms).

Figures 10, 11:
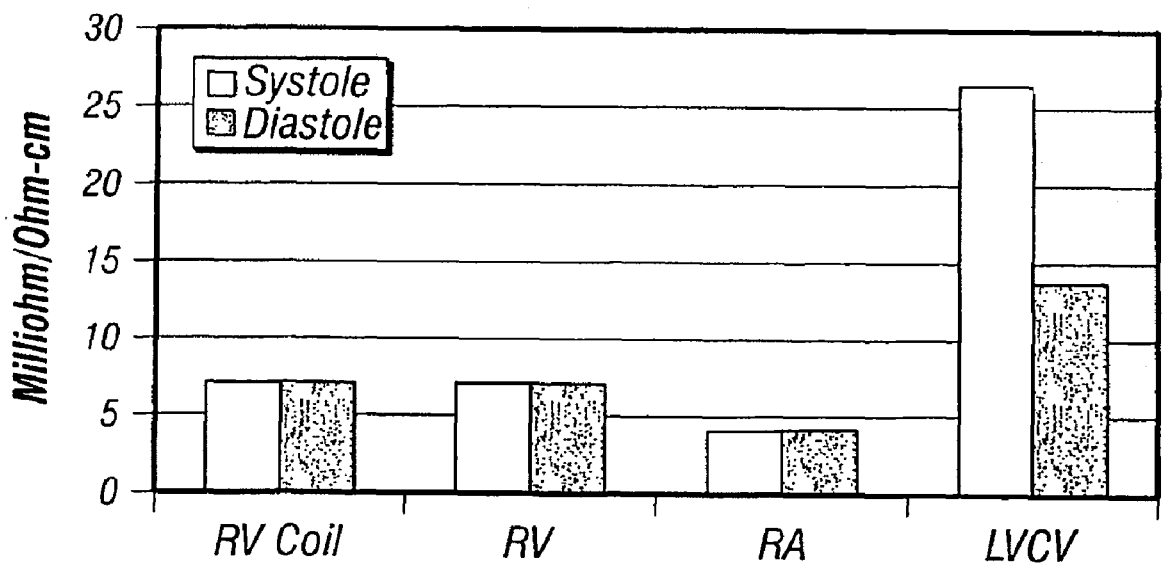
FIG. 10 is a table of simulation results.
FIG. 11 is a chart of the results from FIG. 10.

FIG. 10 shows a table of simulation results, derived using the computer model discussed above, which highlights advantages of the invention. The table lists simulation results for four measurement configurations (RV coil, RV, RA, LVCV) at both end-systole, and at end-diastole for both a normal patient and an edematous patient. The model assumes a left-sided device implant (that is, with the device's housing in the left pectoral region of the patient's chest), and a tripolar electrode configuration. The RV coil configuration uses an implanted defibrillator device with a defibrillation lead in the right ventricle. The other three configurations use an implanted pacemaker device with a lead placed in the left ventricular coronary vein location (LVCV), the right atrial location (RA), and the previously known right ventricle location (RV).

The model simulates pulmonary edema by gradually decreasing the resistivity of volumes corresponding to lung tissue, for example, from 1400 ohm-cm (healthy) down to 350 ohm-cm (edema). As seen in the table, for a given configuration, impedance measurements for an edematous patient are less than the corresponding measurement for a normal patient. For example, a normal patient has an impedance measurement of 84.64 ohms at end-systole with the LVCV configuration, versus a measurement of 56.76 ohms for an edematous patient, a difference of 27.87 ohms, or 32.9%. This corresponds to a sensitivity of 26.55 milliohms/ohm-cm. Sensitivity values are calculated by dividing the impedance change (delta Z) by the change in lung tissue resistivity (not shown in table), and are similarly derived for the other configurations. Published clinical data on baseline (healthy) impedance values and percentage impedance change after edema onset for a tripolar measurement configuration using a device implanted on a patient's left side with the RV electrode configuration correlate with the FIG. 10 simulation results for the RV configuration, providing evidence of the validity of the computer model simulation results. See Li Wang et al., *Feasibility of Predicting CHF Hospitalization Using Pacemaker-Based Impedance Sensor in CHF Patients*, Vol. 8, No. 4, Supplement, Journal of Cardiac Failure, August 2002, abstract 297. Furthermore, the model's respiration sensitivity (1 to 2 ohms per liter of tidal volume) also approximate published right ventricle data (1 ohm per liter). See J. A. Hauck, *A Minute Ventilation Sensor Derived from Intra-Thoracic Electric Impedance as a Cardiac Pacemaker Rate Modulator*, MnU-M93-191, 1993, Available at Andersen Library University Archives. See also C. Cole et. al., *Correlation of Impedance Minute Ventilation with Measured Minute Ventilation in a Rate Responsive Pacemaker*, 24(6):989-93, Pacing & Clinical Electrophysiology, June 2001.

FIG. 11 shows a chart of the sensitivity values from the table of FIG. 10 for each of the four configurations, both at end-systole and at end-diastole. As seen in FIGS. 10 and 11, the LVCV configuration measured at end-systole provides about a 3× increase in sensitivity over the previously known RV configuration. Notice also the difference in sensitivity for the LVCV configuration between end-systole (26.55 milliohm/ohm-cm) and end-diastole (13.69 milliohm/ohm-cm). This sensitivity improvement in excess of 90% at end-systole is a surprising result, and similar results are not seen with the other configurations. One possible explanation may be that at the end of contraction the ventricular heart muscles are thicker and less perfused with blood, thereby providing higher impedance between the epicardial LVCV electrodes and the relatively conductive pool of blood within the heart's chambers. As such, the current preferably flows through the lung tissue, as desired. In contrast, for each of the other configurations the electrodes are intra-cardiac (that is, located within a heart chamber), and current tends to flow through the blood, which always surrounds such electrodes.

Figures 12, 13:
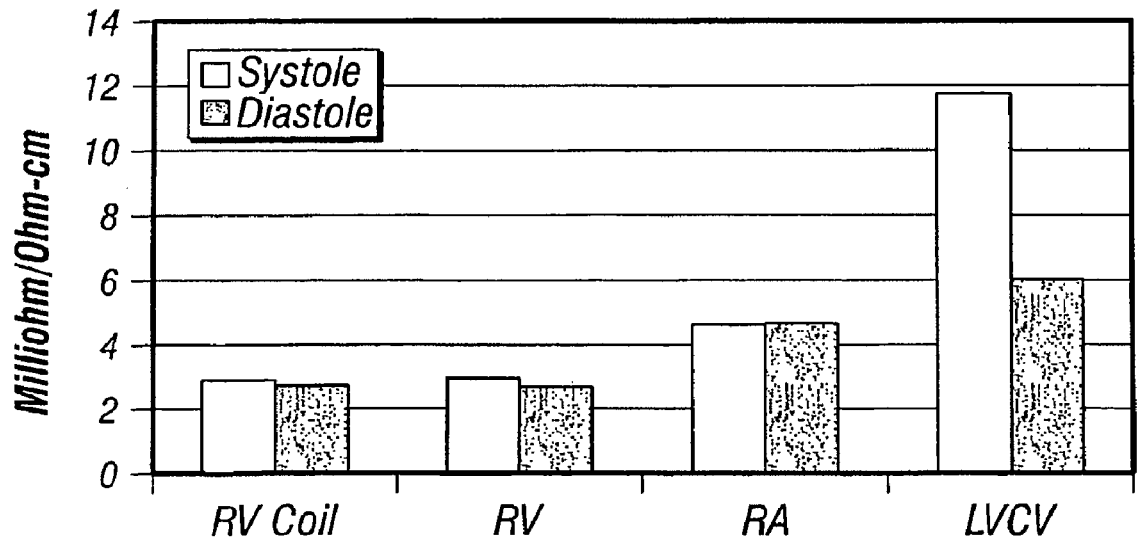
FIG. 12 is another table of simulation results.
FIG. 13 is a chart of the results from FIG. 12.

FIG. 12 shows another table of simulation results, derived using the computer model discussed above, which further highlights advantages of the invention. FIG. 12 is similar to FIG. 10, but assumes a right-sided pectoral device implant with a tripolar electrode measurement configuration. As before, the table lists simulation results for the four measurement configurations (RV coil, RV, RA, LVCV) at both end-systole, and at end-diastole for both a normal patient and an edematous patient.

Using these parameters, a normal patient has an impedance measurement of 36.76 ohms at end-systole with the LVCV configuration, versus a measurement of 24.43 ohms for an edematous patient, a difference of 12.33 ohms, or 33.5%. This corresponds to a sensitivity of 11.74 milliohms/ohm-cm. Similarly, a normal patient has an impedance measurement of 22.40 ohms at end-diastole with the RA configuration, versus a measurement of 17.48 ohms for an edematous patient, a difference of 4.92 ohms, or 22.0%, corresponding to a sensitivity of 4.69 milliohms/ohm-cm. Sensitivity values are similarly derived for the other configurations.

FIG. 13 shows a chart of the sensitivity values from the table of FIG. 12 for each of the four configurations, both at end-systole and at end-diastole. As seen in FIGS. 12 and 13, the LVCV configuration measured at end-systole provides about a 3× increase in sensitivity over the previously known RV configuration, which is similar to the left-sided device implant results of FIGS. 10 and 11. Additionally, the RA configuration provides about a 1.6× increase in sensitivity over the RV configuration. As before, the marked sensitivity difference between end-systole and end-diastole for the LVCV configuration is present.

It is understood by those skilled in the art that the exact numbers presented above and in FIGS. 8-13 correspond to a particular patient simulation and geometry. Variations in the numbers are possible with differing body size, implant sites, anatomical variations, weight, etc. However, as suggested by the two simulations of FIGS. 10-13, the proportional advantage of sensitivity is maintained, with the LVCV configuration showing the same factor of three improvement over the conventional RV configuration.

Figure 14:
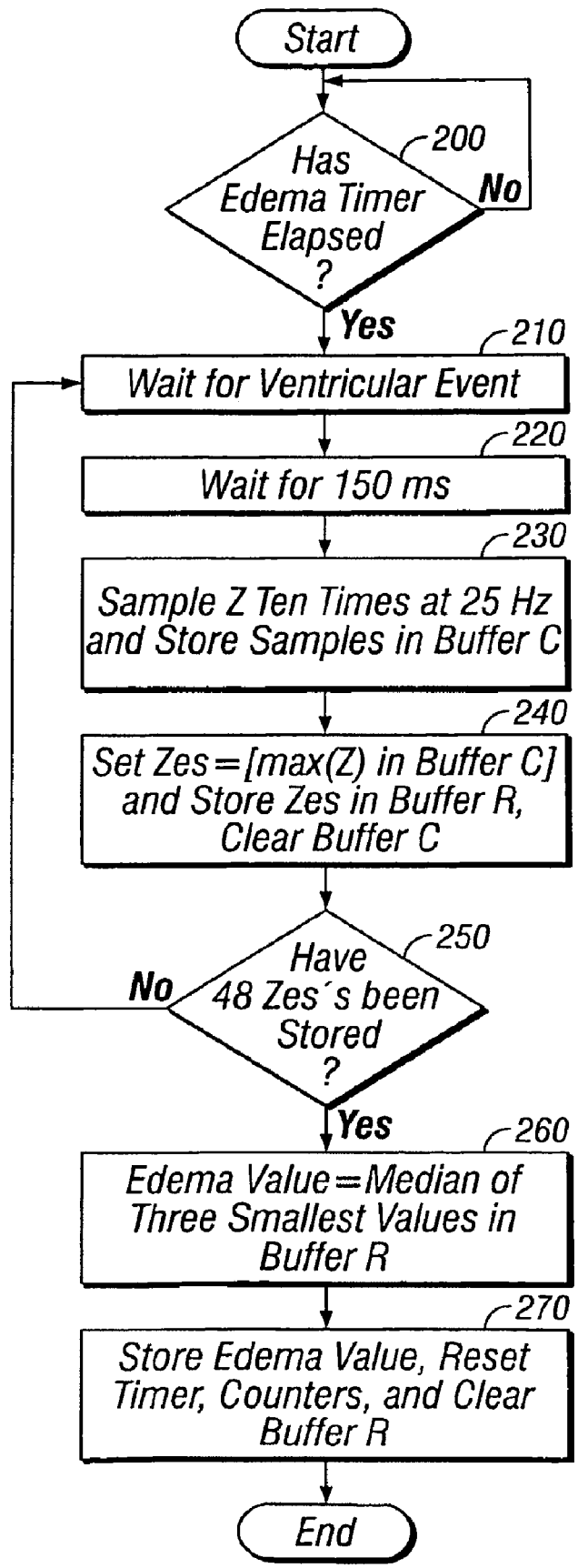
FIG. 14 is a flowchart illustrating an example of how the device of FIG. 5 may make edema assessments.

The flowchart of FIG. 14 shows an example of how an algorithm may be implemented in the control block 76 of FIG. 5 to make edema assessments. The process performed by a control block processing unit executing instructions begins, at step 200, with an edema timer (located within control block 76 in the processing unit, for example) implementing a waiting period. This period may be from about 2 hours to about 3 days, as determined by a physician. The value may be programmable over a radio frequency link to telemetry block 84 (FIG. 5).

Referring again to FIG. 14, after the waiting period has elapsed, the control block 76 waits for the next ventricular event in step 210. The ventricular event may be determined using pace timing control information resident in the control block 76, or from the sense amplifier 94 in the left ventricular sensing/pacing circuit 90 (FIG. 5). The occurrence of a ventricular event indicates that the heart has started its contraction, and prompts a waiting period of about 150 ms in step 220 to allow cardiac contraction to set in. Next, in step 230, impedance is sampled ten times at a rate of 25 Hz, and the impedance samples are stored in a memory buffer C (for cardiac). This allows impedance to be sampled before and after the peak 148 of the impedance waveform (FIG. 8), so as to encounter and determine its peak value, here referred to as Zes (Z at end-systole). Zes is set equal to the largest of the ten impedance samples in buffer C and stored in a memory buffer R (for respiration), and buffer C is cleared at step 240.

At step 250, a counter determines whether 48 Zes's have yet been stored. If not, steps 210-240 are repeated. In this manner, steps 210-240 are repeated 47 times, thereby allowing 48 end-systole impedance measurements Zes to be stored in buffer R, sufficient for covering at least about three breath cycles. Next, at step 260, a pulmonary edema value is assigned the median of the three smallest impedance values (that is, the values corresponding to end-expiration) in buffer R. The pulmonary edema value may be stored in memory, buffer R may be cleared, and the appropriate timers and counters reset, and the process ends. The process may then begin again at step 200, waiting until the next edema sampling moment.

The edema value may be compared with a stored edema threshold value, perhaps programmable over the telemetry link, and if the edema value exceeds the threshold value, a warning flag may be set, or an alarm triggered. Stored edema values or impedance values may then be transmitted by telemetry block 84 to monitoring station 88 (FIG. 5), for example, when the monitoring station 88 interrogates the device 30. A physician might subsequently analyze the data for trends in edema values. A similar algorithm for measuring impedance at a right atrial location may be implemented. An appropriate measurement moment for maximum sensitivity for a right atrial location may be at both end-expiration, and at end-diastole, based on the results from FIGS. 12 and 13. Or, given the insight provided by the ventricular results, at the end of atrial systole, the moment when the atria contain less blood.

Many alternatives are possible for the algorithm. For example, a different number of samples may be taken, mean averaging may be used in place of median, alternate waiting periods may be chosen, and alternate comparison schemes may be implemented. For example, a single register may be used in place of buffers and, concurrent with sampling, the newly sampled measurement may be compared with an ongoing maximum/minimum value stored in the register. As an alternative to waiting periods, a patient may initiate a series of measurements, for example, with a magnet. Impedance values and sensor information may be used to assign an edema value that differs from the measured impedance. Of course, time stamps could also be stored with the edema values, as well as other relevant information, such as posture information, heart rate, or activity levels, for example. Telemedicine home stations could also initiate a measurement, and then send results to a care center.

Referring again to the FIG. 8 waveform 140, it can be seen by those skilled in the art that the end-systolic Zo measurement 144 may be influenced by variations in end-systolic volumes in the heart chambers and great vessels. In the body, these volumes change according to heart rate and posture. Such changes may thus influence the value of Zo 144 that is measured. Therefore, in one implementation, edema may be assessed at about the same heart rates and postures. One way this could be accomplished is by executing the steps of the FIG. 14 flowchart only when the heart rate and posture fall within pre-programmed ranges (that is, the steps of the flowchart would be executed only when the heart rate and posture are about the same as when the last edema assessment was done). Alternatively, the edema assessments could be stored in memory, along with the corresponding heart rate and posture information, using the process of FIG. 14. The edema measurements could then later be classified in bins by heart rate range or posture categories, and transmitted or presented to the physician per the category that he/she selects.

Referring again to FIG. 8, it is evident that the cardiac component of the impedance signal 140 is modulated by respiration, such that its amplitude is less during expiration and greater during inspiration. For systems that measure stroke volume changes by impedance using LVCV leads (while optimizing pacing parameters, for example), it would be advantageous to account for this modulation. Otherwise, the stroke volume measurement may contain error. One way to compensate is by taking stroke volume measurements at end inspiration only, for example.

A number of embodiments of the invention have been described. Nevertheless, it will be understood that various modifications may be made without departing from the spirit and scope of the invention. Accordingly, other embodiments are within the scope of the following claims.

What is claimed is:

1. An implantable medical device comprising:
a housing for the implantable device sized for implantation in a chest region of a patient and comprising a housing electrode;
a left ventricular lead port into which a proximal end of a lead is connectable, the lead having first and second conductors that are insulated from one another and that extend from the proximal end of the lead to corresponding first and second electrodes positioned near a distal end of the lead;
an electrical impedance measurement circuit electrically connected to the left ventricular lead port and to the housing electrode, the circuit adapted to inject current between the first lead electrode and the housing electrode, and adapted to measure a voltage potential between the second lead electrode and the housing electrode, the voltage potential created by the current injection; and
a control module adapted to calculate a series of multiple impedance value samples over a period of time, each impedance value sample being calculated based on a measurement of the voltage potential and the current injection that created the voltage potential, and to select and store in memory of the implantable device baseline impedance value samples from the series of multiple samples, wherein the baseline impedance value samples are selected based on the selected sample corresponding to a predetermined moment of both the cardiac cycle and the respiration cycle of the patient.

2. The device of claim 1, wherein the control module is further adapted to make an edema assessment using one or more of the baseline impedance value samples and a stored edema threshold impedance value.

3. The device of claim 2, wherein the stored edema threshold value is a value programmable by telemetry link.

4. The device of claim 3, wherein the control module is further adapted such that the edema assessment comprises comparing the one or more of the baseline impedance value samples to the stored edema threshold value.

5. The device of claim 4, wherein the control module is further adapted to trigger a warning flag to be set if the one or more of the baseline impedance value samples exceeds the stored edema threshold value.

6. The device of claim 1, wherein the predetermined moment of the cardiac cycle comprises end-systole.

7. The device of claim 6, wherein the predetermined moment of the respiration cycle comprises end-expiration.

8. The device of claim 1, wherein the measurement circuit is adapted to take, during a respiration cycle, multiple measurements each at a different one of consecutive cardiac cycles at end of systole.

9. The device of claim 8, wherein the control module is adapted such that the selecting baseline impedance value samples comprises selecting a minimum voltage potential measure from the measured voltage potentials taken at end of systole during the respiration cycle.

10. The device of claim 9, wherein the control module is adapted to select baseline impedance value samples over multiple respiration cycles.

11. The device of claim 1, wherein the control module is further adapted to store in the memory of the medical device multiple baseline impedance value samples from different times.

12. The device of claim 11, wherein the different times are determined by an edema timer within the medical device, wherein the timer establishes a period of time between obtaining consecutive ones of the baseline impedance value samples to be within a range of about two hours to about three days.

13. The device of claim 11, further comprising a telemetry circuit adapted to telemeter the multiple baseline impedance value samples to an external receiver for analysis.

14. The device of claim 1, further comprising a lead having first and second conductors that are insulated from one another and that extend from the proximal end of the lead to corresponding first and second electrodes positioned near a distal end of the lead.

15. The device of claim 14, wherein the first and second electrodes are configured for positioning within a left ventricular coronary vein.

16. The device of claim 15, wherein the first and second electrodes are, respectively, first and second epicardial electrodes.

17. The device of claim 16, wherein the electrical impedance measurement circuit is adapted to inject electrical current between the first epicardial lead electrode and the housing electrode, and is adapted to measure a voltage potential created thereby between the second epicardial lead electrode and the housing electrode to make a voltage potential measurement.

18. The device of claim 17, wherein the epicardial electrodes are configured to be sutured to a wall of a left ventricle.

19. The device of claim 1, wherein the impedance measurement circuit is adapted to measure the voltage potential at a specified heart rate range.

20. The device of claim 1, wherein the impedance measurement circuit is adapted to measure the voltage potential at a specified posture of the patient, as determined by a posture sensor.

21. The device of claim 1, wherein the housing electrode is a can electrode.

22. The device of claim 1, wherein the housing electrode is a header electrode.

23. The device of claim 1, further comprising a second lead port into which a proximal end of a second lead is connectable, the second lead having first and second conductors that are insulated from one another and that extend from the proximal end of the lead to corresponding first and second electrodes positioned near a distal end of the lead; and
wherein the electrical impedance measurement circuit is further electrically connected to the second lead port, and is adapted to inject current between the first lead electrode of the second lead and the housing electrode, and is adapted to measure a second voltage potential between the second lead electrode of the second lead and the housing electrode, the second voltage potential created by the current injection; and
wherein the control module is further adapted to calculate a second impedance value based on the second voltage potential and the current injection.

24. A system for monitoring pulmonary edema in a human being, the system comprising:
means for injecting an electrical current between a first electrode located in a coronary vein of a left ventricle and a housing of a medical device implanted in a chest region;
means for measuring a voltage potential between a second electrode located in the coronary vein of the left ventricle and the medical device housing, the voltage potential created by the electrical current injection; and
means for assessing pulmonary edema based on a baseline impedance value sample, the baseline impedance value sample selected from a series of multiple impedance values sampled over a period of time, each of the multiple impedance values being calculated based on a measurement of the voltage potential and the injected electrical current that created the voltage potential, wherein the baseline impedance value sample is selected based on the selected sample corresponding to a predetermined moment of both the cardiac cycle and the respiration cycle of the human being.

25. The system of claim 24, further comprising means for calculating an impedance value by taking a ratio of the measured voltage potential to the injected current.

26. A system for monitoring pulmonary edema in a human being, the system comprising:
means for injecting a first electrical current between a first electrode located in a coronary vein of a left ventricle and a housing of a medical device implanted in a chest region;
means for measuring a first voltage potential between a second electrode located in the coronary vein of the left ventricle and the medical device housing, the first voltage potential created by the first current injection;
means for injecting a second electrical current between a third electrode located in a right atrium and the medical device housing;
means for measuring a second voltage potential between a fourth electrode located in the right atrium and the medical device housing, the second voltage potential created by the second current injection; and
means for assessing pulmonary edema based on a stored edema threshold impedance value and a baseline impedance value sample, the baseline impedance value sample selected from a series of multiple impedance values sampled over a period of time, each of the multiple impedance values being calculated based on one or more of (i) a measurement of the first voltage potential and the first injected electrical current that created the first voltage potential, and (ii) a measurement of the second voltage potential and the second injected electrical current that created the second voltage potential, wherein the baseline impedance value is selected based on the selected sample corresponding to a predetermined moment of both the cardiac cycle and the respiration cycle of the human being.

27. The system of claim 26, further comprising:
means for calculating a first impedance value by taking a first ratio of the measured first voltage potential to the injected first current; and
means for calculating a second impedance value by taking a second ratio of the measured second voltage potential to the injected second current.

28. The system of claim 26, wherein a weighted combination of the an impedance sampled from the coronary vein of the left ventricle and an impedance sampled from the right atrium is used to assess pulmonary edema.

* * * * *

UNITED STATES PATENT AND TRADEMARK OFFICE
CERTIFICATE OF CORRECTION

PATENT NO. : 8,131,356 B2
APPLICATION NO. : 11/936357
DATED : March 6, 2012
INVENTOR(S) : Andres Belalcazar It is certified that error appears in the above-identified patent and that said Letters Patent is hereby corrected as shown below:

Column 14, line 57, Claim 28, before "an," delete "the."

Signed and Sealed this
Fifth Day of June, 2012

David J. Kappos
*Director of the United States Patent and Trademark Office*